US011147509B2

(12) United States Patent
Rousseau et al.

(10) Patent No.: US 11,147,509 B2
(45) Date of Patent: Oct. 19, 2021

(54) METHOD FOR CUSTOMIZING A MOUNTED SENSING DEVICE

(71) Applicant: Essilor International, Charenton-le-Pont (FR)

(72) Inventors: Denis Rousseau, Charenton-le-Pont (FR); Marie Lore, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 260 days.

(21) Appl. No.: 15/557,321

(22) PCT Filed: Mar. 9, 2016

(86) PCT No.: PCT/EP2016/055021
§ 371 (c)(1),
(2) Date: Sep. 11, 2017

(87) PCT Pub. No.: WO2016/142423
PCT Pub. Date: Sep. 15, 2016

(65) Prior Publication Data
US 2018/0049697 A1 Feb. 22, 2018

(30) Foreign Application Priority Data
Mar. 12, 2015 (EP) .................................... 15305377

(51) Int. Cl.
*A61B 5/00* (2006.01)
*G06F 3/01* (2006.01)
(Continued)

(52) U.S. Cl.
CPC ........ *A61B 5/6803* (2013.01); *G02B 27/0093* (2013.01); *G02B 27/017* (2013.01);
(Continued)

(58) Field of Classification Search
CPC ... G02B 27/0093; G02C 11/10; A61B 5/6803; G06F 3/013; G06F 3/012; G06F 3/014
See application file for complete search history.

(56) References Cited

U.S. PATENT DOCUMENTS 6,198,394 B1 * 3/2001 Jacobsen ............... A61B 5/1112
340/573.1
8,862,715 B1 10/2014 Tom et al.
(Continued)

OTHER PUBLICATIONS

International Search Report dated Apr. 20, 2016 in PCT/EP2016/055021, filed on Mar. 9, 2016.

*Primary Examiner* — William L Bashore
*Assistant Examiner* — Gregory A Distefano
(74) *Attorney, Agent, or Firm* — Oblon, McClelland, Maier & Neustadt, L.L.P.

(57) ABSTRACT

A method for customizing a mounted sensing device including a first set of similar or identical sensors having different location and/or orientation, each sensor configured to measure at least one first parameter relating to a wearer of the mounted sensing device, the method including: a sensor selecting during which at least one of the sensors is selected to be used to measure the at least one first parameter, wherein the at least one selected sensor is selected among the first set of similar or identical sensors based on wearer data indicative of morphology of the wearer, and based on
(Continued)

their respective location and/or orientation such that the selected at least one sensor is a most appropriate for the wearer and/or for measuring the at least one first parameter.

14 Claims, 2 Drawing Sheets

(51) Int. Cl.
    *G02B 27/00*     (2006.01)
    *G02C 11/00*     (2006.01)
    *G02B 27/01*     (2006.01)
    *G06F 3/038*     (2013.01)
    *G06F 1/16*     (2006.01)
    *G06F 1/3206*     (2019.01)

(52) U.S. Cl.
    CPC .............. *G02C 11/10* (2013.01); *G06F 1/163* (2013.01); *G06F 1/3206* (2013.01); *G06F 3/012* (2013.01); *G06F 3/013* (2013.01); *G06F 3/015* (2013.01); *G06F 3/038* (2013.01); *G02B 2027/0178* (2013.01); *G06F 3/014* (2013.01)

(56) References Cited

U.S. PATENT DOCUMENTS

| | | | |
|---|---|---|---|
| 2009/0326406 A1* | 12/2009 | Tan | G06F 3/015 |
| | | | 600/546 |
| 2010/0004977 A1* | 1/2010 | Marci | A61B 5/16 |
| | | | 705/7.32 |
| 2010/0110368 A1 | 5/2010 | Chaum | |
| 2011/0254760 A1* | 10/2011 | Lloyd | G06F 3/0346 |
| | | | 345/156 |
| 2014/0118243 A1 | 5/2014 | Kim | |
| 2014/0145914 A1 | 5/2014 | Latta et al. | |
| 2014/0160424 A1 | 6/2014 | Benko et al. | |
| 2015/0029088 A1 | 1/2015 | Kim et al. | |
| 2015/0062022 A1 | 3/2015 | Rabii | |
| 2015/0282768 A1* | 10/2015 | Luna | A61B 5/721 |
| | | | 600/301 |
| 2016/0025975 A1 | 1/2016 | Rabii | |
| 2016/0162022 A1* | 6/2016 | Seth | G06F 3/014 |
| | | | 345/156 |
| 2017/0112393 A1* | 4/2017 | Tougasaki | A61B 5/742 |

* cited by examiner

METHOD FOR CUSTOMIZING A MOUNTED SENSING DEVICE

FIELD OF THE INVENTION

The invention relates to a method for customizing a mounted sensing device comprising a first set of similar or identical sensors having different location and/or orientation, each sensor being adapted to measure at least one first parameter relating to the wearer of the mounted sensing device. The invention further relates to a mounted sensing device.

BACKGROUND OF THE INVENTION

More and more mounted devices comprise sensors adapted to measure parameters relating to the wearer or the environment of the wearer.

Such measured parameters may be used to adapt the mounted device.

Increasing the accuracy of the measurements performed by such sensors is important to be able to use such measurements either to perform statistical studied or event generate accurate information concerning the wearer and/or the environment.

A way of increasing the accuracy of the measurements is to improve the accuracy of the sensors them self.

However, a specificity of having sensors mounted on a mounted sensing device is that the sensing conditions are unstable. The mounted sensing device may move relative to the user and the environment may change quickly and be very diverse.

Therefore, even using very accurate sensors the overall measurements may not be very accurate in particular because of the specific measurements condition linked to the fact that the sensors are mounted on a mounted sensing device to be mounted on a wearer, for example on the head or wrist of the wearer.

Thus there is a need for a method for increasing the accuracy of the measurements performed by sensors mounted on mounted sensing devices.

One object of the present invention is to provide such a method.

SUMMARY OF THE INVENTION

To this end, the invention proposes a method, for example implemented by computer means, for customizing a mounted sensing device comprising a first set of similar or identical sensors having different location and/or orientation, each sensor being adapted to measure at least one first parameter relating to the wearer of the mounted sensing device.

The method according to the invention comprising a sensor selecting step during which at least one of the sensors is selected to be used to measure the at least one first parameter, wherein the at least one selected sensor is selected among the first set of similar or identical sensors based on wearer data indicative of the morphology of the wearer, and based on their respective location and/or orientation such that said selected at least one sensor is the most appropriate for the wearer and/or for measuring the at least one first parameter.

Advantageously, providing a mounted sensing device with a plurality of similar or identical sensors having different locations and/or orientations and selecting the most appropriate sensor based on the location and/or orientation of the sensors allows increasing the accuracy of the measured parameter.

Indeed, the inventors have observed that depending on the parameter to be measured and the wearer the position and/or orientation of the sensor may greatly influence the accuracy of the measured parameter.

The invention proposes to provide a mounted sensing device, for example a head mounted sensing device, with a set of similar sensors and to customize such mounted sensing device by selecting the most appropriate sensor(s).

Such solution appears more appropriate financially than trying for each wearer to determine the best position and/or orientation of the sensor(s) and providing a mounted sensing device with such customized sensors. Indeed, the method according to the invention allows customizing "universal" mounted sensing devices.

Furthermore the method according to the invention allows adjusting in real time the most appropriate sensor(s) among the set of sensors.

According to further embodiments which can be considered alone or in combination:
- the mounted sensing device is a head mounted device and/or a wrist mounted device; and/or
- during the selecting step the at least one selected sensor is selected based on application data indicative of the application of the measured parameter; and/or
- during the selecting step the at least one sensor is selected by measuring the at least one parameter with each of the plurality of sensors and by selecting the sensors providing the most accurate measure; and/or
- the wearer data comprise at least morphology data relating to the morphology of the contact areas of the wearer, for example of the contact area of the wearer's head or of the wearer's wrist, and the mounted sensing device; and/or
- during the selecting step the at least one sensor is selected based on position data indicative to the position of the mounted sensing device relative to the wearer, for example the head of the wearer; and/or
- during the selecting step a specific spatial distribution of sensors is selected; and/or
- during the selecting step a plurality of sensors are selected and wherein the method further comprises a distribution frequency determining step during which a distribution of frequencies of the measurements implemented by each sensor of the plurality of selected sensors is determined based at least on the at least one parameter intended to be measured; and/or
- the mounted sensing device further comprises a second set of similar sensors having different location and/or orientation and being adapted to measure at least one second parameter relating to the wearer of the mounted sensing device, the second parameter being different than the first parameter, and during the selecting step at least one sensor from the second set of sensors is selected so that the location and/or orientation of the selected at least sensor is the most appropriate of the second set of sensors for the wearer and/or for measuring the at least one second parameter; and/or
- the sensors comprise sensors, for example eye tracking sensors, arranged to measure the gazing direction or the wearer and/or the eyelid beat of the wearer and/or the pupil dilation of the wearer; and/or
- the sensors comprise sensors, for example capacitive sensors, configured to measure the contact area or the distance between the mounted sensing device and the wearer, for example the wearer's head; and/or the sensors comprise sensors, for example resistive sensors, configured to measure biological and/or physiological parameters of the wearer; and/or the sensors comprise optical blood pressure or blood analysis sensor, for example heart beat or oxymetry measurement and/or pressure sensor.

According to a further aspect, the invention relates to a mounted sensing device comprising:

a plurality of similar or identical sensors having different location and/or orientation, each sensor being adapted to measure at least one parameter relating to the wearer of the mounted sensing device, a non-transitory computer-readable medium, and program instructions stored on the non-transitory computer-readable medium and executable by at least one processor to select at least one of the sensors having the location and/or orientation the most appropriate of the plurality of sensors for the wearer and/or for measuring the at least one parameter based on wearer data indicative of the morphology of the wearer.

The wearer data may comprise at least morphology data relating to the morphology of the contact areas of the wearer, for example the contact areas of the wearer's head or of the wearer's wrist, and the mounted sensing device.

The mounted sensing device may further comprising a communication unit configured to receive an application data indicative of the application of the measured parameter and wherein the processor is further configured to select the most appropriate sensor based on the application data.

The mounted sensing device may be a head mounted device. The sensors may be integrated into the frame of the head mounted device.

The mounted sensing device may be a wrist sensing device.

The invention further relates to a computer program product comprising one or more stored sequences of instructions that are accessible to a processor and which, when executed by the processor, causes the processor to carry out the steps of the method according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

In the sense of the invention a "mounted sensing device" corresponds to any device arranged to be mounted on a wearer, the device comprise a set of sensors. Although in the following description focuses on a head mounted device, the mounted sensing device is not limited to such head mounted device and can be a wrist mounted device, a hand mounted device, a foot mounted device or any device comprising sensors and arranged to be mounted on a wearer.

Figure 1:
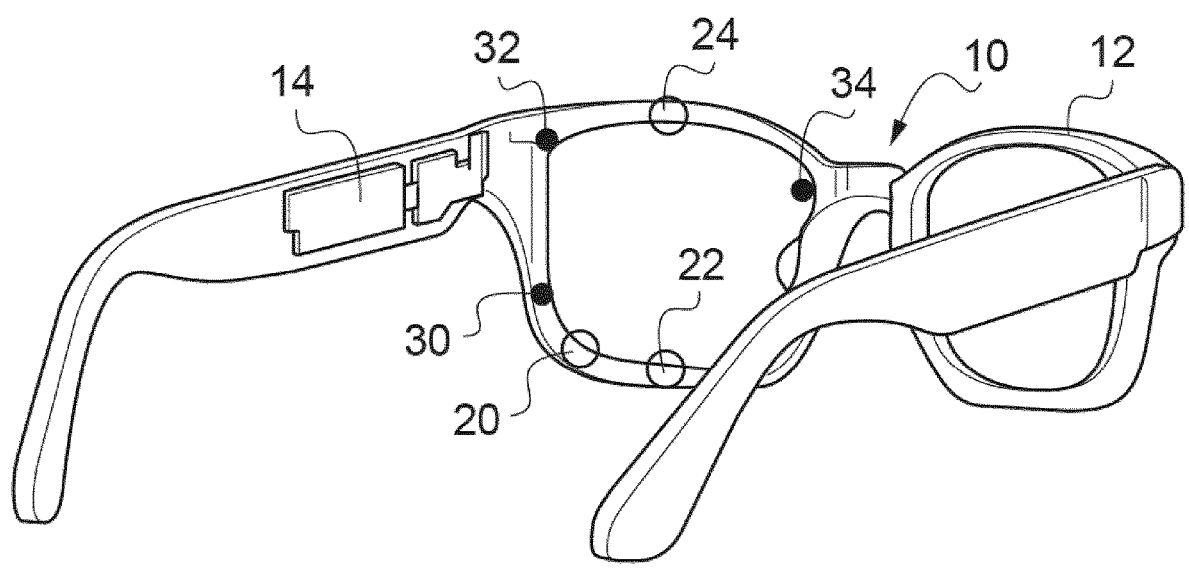
FIG. 1 is a schematic representation of an head mounted device according to an embodiment of the invention.

FIG. 1 represents an example of head-mounted device 10 comprising a first set of similar 20, 22, 24 sensors having different location and/or orientations. In the sense of the invention, the term "similar sensors" refers to sensors which sense the same type of parameter, and more precisely analogous parameters. For instance, a CCD sensor and a CMOS sensor are considered as "similar sensors" since both sensors may acquire images. The head mounted device 10 comprises a spectacle frame 12 and the sensors are mounted on the spectacle frame 12.

Although the method of the invention is not limited to such type of head-mounted devices, it appears to be particularly advantageous for head mounted devices comprising a spectacle frame.

Indeed, the inventors have observed that the method according to the invention increases the accuracy of the sensors of the head mounted device, in particular of eye tracking devices arranged in spectacle frames.

The head mounted device 10 represented on FIG. 1 comprises a spectacle frame 12 with three sensors, for example three cameras 20, 22, 24, directed at the left eye (not shown) of the wearer. The cameras 20, 22, 24 are arranged to be directed toward the head in order to track the locations of the eyes of the wearer and/or the structures of the eyes of the wearer, for example the pupils, eyelids, irises, glints, and/or other reference points in the region of the eye(s).

The cameras 20, 22, 24 may include charge-coupled device (CCD), complementary metal-oxide-semiconductor (CMOS), or other photodetectors that include an active area, e.g., including a rectangular or linear or other array of pixels, for capturing images and/or generating video signals representing the images. The active area of each of the cameras 20, 22, 24 may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

The three cameras have different orientations and positions on the spectacle frame.

The head mounted device 10 may further comprise three illumination sources 30, 32, 34 arranged so as to illuminate the left eye of the wearer when wearing the spectacle frame 12.

The three illumination sources 30, 32, 34 are fixed to the spectacle frame 12. In an exemplary embodiment, illumination sources 30, 32, 34 may include light-emitting diodes (LEDs), organic LEDs (OLEDs), laser diodes, or other devices that convert electrical energy into photons. Each illumination source 30, 32, 34 may be used to illuminate the eye to acquire images using any of the cameras 20, 22, 24 and/or to produce reference glints for measurement purposes to improve gaze-tracking accuracy. In an exemplary embodiment, each light source 30, 32, 34 may be configured for emitting a relatively narrow or wide bandwidth of the light, for example infrared light at one or more wavelengths between about 700-1000 nanometers. For example, AlGaAs LEDs provides an emission peak at 850 nm and are widely used and affordable, while commodity CMOS cameras used in mobile phones and webcams show a good sensibility at this wavelength.

The head mounted device 10 may further comprise a processing unit 14 arranged to receive the parameter sensed by the sensors 20, 22, 24, for example images collected by the cameras 20, 22, 24. The processing unit may be arranged in one of the sides of the spectacle frame.

According to an embodiment of the invention, the head mounted device further comprises a non-transitory computer-readable medium, at least one processor, and program instructions stored on the non-transitory computer-readable medium and executable by the at least one processor to select at least one of the sensors having the location and/or orientation the most appropriate of the plurality of sensors for the wearer and/or for measuring the at least one parameter.

Figure 2:
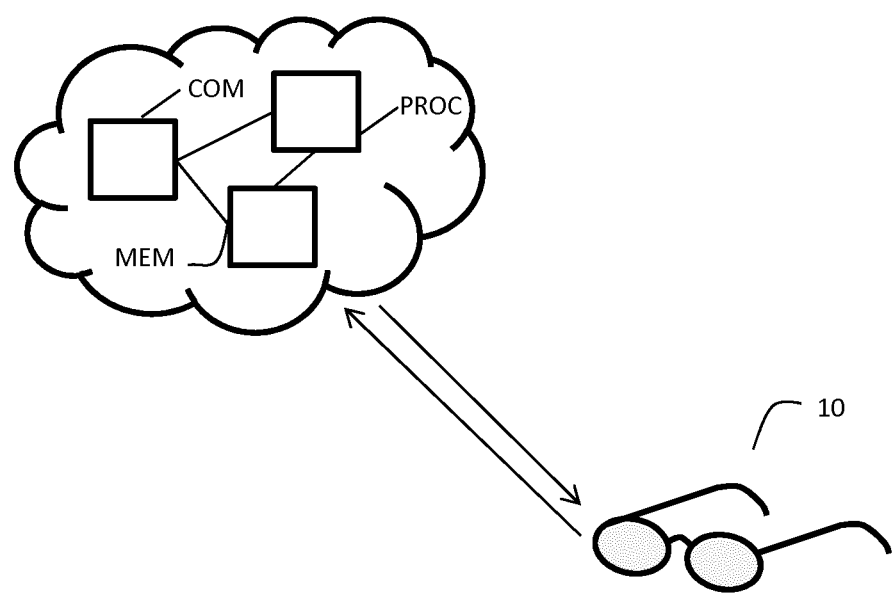
FIG. 2 represents a networked data-processing device according to the invention.

According to an embodiment of the invention, illustrated on FIG. 2, the head mounted device communicates with a distant entity.

For example, the head mounted device may further comprise a communication unit configured to communicate with a distance entity either to store the measured parameter in a memory MEM or to select at least one of the sensors having the location and/or orientation the most appropriate of the plurality of sensors for the wearer and/or for measuring the at least one parameter.

Typically, the distance entity comprises a communication unit COM configured to communicate at least with the head mounted device, a memory MEM, at least one processor PROC and program instructions stored on the non-transitory computer-readable medium and executable by the at least one processor to select at least one of the sensors having the location and/or orientation the most appropriate of the plurality of sensors for the wearer and/or for measuring the at least one parameter.

The distance entity can include different computing objects such as personal digital assistants, audio/video devices, mobile phones, MPEG-1 Audio Layer 3 (MP3) players, personal computers, laptops, tablets, bluetooth headset, watch, wristband, etc. . . .

Each computing object and the head mounted device can communicate with one or more other by way of a communication network, either directly or indirectly. Even though illustrated as a single element in FIG. 2, network can include other computing objects and computing devices that provide services to the system of FIG. 2, and/or can represent multiple interconnected networks, which are not shown.

In a network environment in which the communications network/bus can be the Internet, the computing objects can be Web servers, file servers, media servers, etc. with which the client computing objects or devices communicate via any of a number of known protocols, such as the hypertext transfer protocol (HTTP).

Although not represented, the head mounted device may further comprise a power source, for example a battery and/or other electronics. Advantageously, to distribute weight more evenly within the spectacle frame 12, the power source and/or other electronics may be arranged in the side of the spectacle frame opposite to the one containing the processing unit 14.

Advantageously, such head mounted device comprising sensors included in a spectacle frame the wearer may use the head mounted device over long periods without being hindered, for example on the everyday base.

Although on FIG. 1 cameras and illumination sources have been represented only on the left side of the spectacle frame, the head mounted device may very well comprise sensors and/or on the right side of the spectacle frame.

Advantageously, having sensors on both sides of the spectacle frame allows providing accurate information, for example on the gazing direction and distance of the wearer.

Although the head mounted device represented on FIG. 1 comprises eye trackers, the sensors of the head mounted device according to the invention may comprise other sensors arranged to measure the gazing direction of the wearer According to an embodiment of the invention, the sensors may be configured to measure the contact area or the distance between the head mounted device and the wearer's head, for example the sensors may be capacitive sensors.

Typically, the frame of the head mounted device may comprise a plurality of capacitive sensors at different positions and orientation. Rather than having all the sensors active, the method according to the invention may be used to select the sensors that are to be active based for example on the position of the head mounted device relative to the head of the wearer.

Advantageously, the method of the invention allows reducing the batteries of the head mounted device since only the most appropriate sensors are activated.

According to an embodiment of the invention, the sensors may be configured to measure biological and/or physiological parameters of the wearer, for example the sensors are resistive sensors. For example the sensors are configured to sense parameter relating to the ametropia of the wearer and/or features of the eyes of the wearer such as pupil diameter, and/or optical blood pressure or blood analysis, for example heart beat or oximetry measurement.

According to an embodiment of the invention, the sensors are configured to measure a parameter relating to the environment of the wearer of the head mounted device. For example, the sensors are configured to measure spectral features and intensity of the light received by the wearer.

According to the method of the invention at least one, for example a plurality, of the sensors is selected to measure the at least one first parameter. The at least one selected sensor is selected among the first set of similar or identical sensors based on their respective location and/or orientation such that said selected at least one sensor is the most appropriate for the wearer and/or for measuring the at least one first parameter.

In a preferred embodiment of the invention, at least one sensor among the first set of similar or identical sensors is not selected as being the most appropriate sensor for the wearer and/or for measuring the at least one first parameter. In other words, not all the sensors of the first set of similar or identical sensors may be selected during the sensor selecting step.

According to an embodiment of the invention, the most appropriate sensor of the first set of similar or identical sensors for the wearer and/or for measuring the at least one first parameter may be determined with tests.

For instance, the most appropriate sensor for the wearer and/or for measuring a first parameter may be determined by comparison of the measurement of each sensor of the first set of similar or identical sensors with a predetermined value. Such predetermined value may be a standard value of the first parameter.

For example, a mounted sensing device comprises a plurality of LEDs having different location and/or orientation. The LEDs are successively turned on for determining which LED is the most appropriate for the wearer and/or for measuring the reflection of the light on the eye of the wearer. The most appropriate LEDs may be determined by comparison of the measurement of each LED with a standard value of the reflection of the light on the eye of the wearer.

The most appropriate sensor may be determined based on the signal to noise ratio. More precisely, the sensors of the set of similar sensors may allow having a signal to noise ratio. The most appropriate sensor among the set of similar sensors may be selected as being the sensor giving the best signal to noise ratio.

The most appropriate sensor may be determined based on a signal after reflection. More precisely, the sensors of the set of similar sensors may comprise a couple of an emitter and a receptor, and several possible combinations of couple of emitter and receptor may be tested. The most appropriate sensor among the set of similar sensors may be selected as being the sensor giving the higher signal after reflection.

The most appropriate sensor for the wearer and/or for measuring a first parameter may also be determined by comparison of the measurement of each sensor of the first set of similar or identical sensors with a range of values. Indeed, since the mounted sensing device may move relative to the wearer, only few sensors of the first set of similar or identical sensors may be well-placed for measuring the first parameter.

For example, in the case where the mounted sensing device is a wristwatch, a plurality of similar or identical pulse sensors may have different location around the wrist. The most appropriate pulse sensor for measuring the pulse may be determined by comparison of the pulse measurement of each pulse sensor with a range of pulse values. The range of pulse values may be, for example, between 50 and 80 pulses per minute. Indeed, since the wristwatch may move around the wrist of the wearer, only few pulse sensors among the first set of similar or identical pulse sensors may be well-placed for allowing obtaining a measure of the pulse of the wearer.

According to an embodiment of the invention, the at least one selected sensor may be selected further based on application data indicative of the application of the measured parameter. Indeed, a given parameter may be used for different applications that may require using a different sensor among the first set of sensors.

For example, depending on the application it may be more relevant to use an eye tracker close to the center of the head mounted device or to use a more off centered eye tracker.

Typically, during the selecting step the at least one sensor is selected by measuring the at least one parameter with each of the plurality of sensors and by selecting the sensors providing the most accurate measurement.

For example, the measurements of the at least one parameter with each of the plurality of sensors may be repeated, at least once, in order to determine the sensors providing the most accurate measurement.

For instance, if the measurements are repeated once, the at least one sensor providing the most accurate measurement may be the sensor with the lowest difference between the two measurements. As another example, if the measurements are repeated at least twice, the at least one sensor providing the most accurate measurement may be the sensor with the lowest standard deviation, the first measurement being selected as the reference for calculating the standard deviation.

Moreover, standard statistical analysis methods may be used to determine the sensor giving the most accurate and repeatable values.

According to an embodiment of the invention, the at least one sensor is selected based on wearer data indicative of the wearer, for example data indicative of the morphology of the wearer. Typically, the wearer data comprise at least morphology data relating to the morphology of the contact areas of the wearer's head and the head mounted device.

The selection step may be carried out as part of an initialization process when the wearer tries on a new head mounted device. A head mounted device comprising a plurality of similar or identical sensors having different location and/or orientation, each sensor being adapted to measure at least one first parameter relating to the wearer of the head mounted device, is provided to the wearer.

At least one of the sensors is selected to be used to measure a parameter of the wearer based for example on the morphology of the wearer. A routine test may be carried out to determine the most appropriate, for example the most accurate, sensor when the head mounted device is worn by the wearer.

The most appropriate sensor among the set of similar sensors may be determined based on direct tests carried out by the similar sensors, or based on a simulation of the measurement with a three-dimensional scanned value of the morphology of the wearer. In other words, the most appropriate sensor may be selected based on direct measurements or on simulated measurements relative to the morphology of the wearer.

The selection of the at least one sensors may be carried out regularly for example each time the wearer starts the sensors or each time the wearer puts the head mounted device on.

According to an embodiment of the invention, the selection of the at least one sensor may be based on position data indicative to the position of the head mounted device relative to the wearer, for example the head of the wearer.

Typically, when the head mounted device moves relative to the head of the wearer, the most appropriate sensor, for example the most accurate sensor, may change and the method of the invention may be implemented to determine the most appropriate sensor based on the new position of the head mounted device.

The position of the head mounted device relative to the wearer may also be used to select the most appropriate sensor, for example the most accurate, during an initializing process.

In a preferred embodiment of the invention, according to the application of the measured parameter and/or to the wearer data comprising for instance morphology data relative to the morphology of the wearer and/or to the position of the sensing mounting device relative to the wearer and/or to the accuracy of the measurements of the sensors, at least one sensor is selected among the first set of similar or identical sensors based on their respective location and/or orientation.

During the selection step a plurality of sensors may be selected.

When selecting a plurality of sensors a specific spatial distribution of the selected sensors may be determined based on the wearer data and/or application data and/or the specific parameter to be measured.

Furthermore, when a plurality of sensors is selected the method may further comprises a distribution frequency determining step during which a distribution of frequencies of the measurements implemented by each sensor of the plurality of selected sensors is determined based at least on the at least one parameter intended to be measured. Typically, when selecting two sensors, one of the two sensors may need to be activated on a lower frequency than the other.

Determining the most appropriate a distribution of frequencies of the measurements implemented by each sensor of the plurality of selected sensors provides a good compromise between the accuracy of the measurements and the energy required to activate the sensors.

For example, if a sensors needs to be activated each 1 second and another sensor may need to be activated only every 2 seconds, having the possibility to determine such distribution of frequencies helps improve the overall efficiency of the head mounted device.

As represented on FIG. 1, the head mounted device may further comprises a second set of similar sensors (having different location and/or orientation and being adapted to measure at least one second parameter relating to the wearer of the head mounted device, the second parameter being different than the first parameter.

During the selecting step at least one sensor from the second set of sensors is selected so that the location and/or orientation of the selected at least sensor is the most appropriate of the second set of sensors for the wearer and/or for measuring the at least one second parameter.

Figure 3:
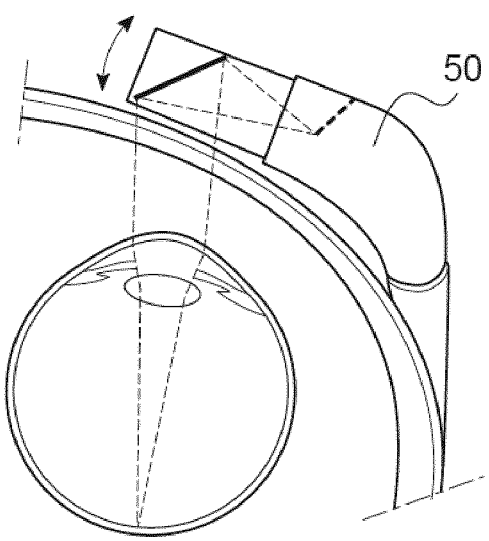
FIG. 3 is a schematic representation of a head mounted device according to a further embodiment of the invention.

As represented on FIG. 3, the head mounted device according to the invention may comprise a virtual image display device 50, preferably allowing the wearer to see both the virtual image and the real world through it. The virtual image display device is able to display graphical images, and an electronic driving system (memory+processor) sends to the virtual display image the image to display. Preferably it is able to display image in different viewing directions.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for customizing a mounted sensing device, the method comprising:
   providing a mounted sensing device including a first set of similar or identical sensors having different locations and/or orientations, each sensor configured to measure at least one first parameter relating to a wearer of the mounted sensing device;
   selecting at least one of the sensors to measure the at least one first parameter; and
   determining a distribution of measurement frequencies implemented by each sensor of the plurality of selected sensors based at least on the at least one parameter intended to be measured;
   wherein the selecting is based on wearer data indicative of morphology of the wearer, and based on respective locations and/or orientations of the sensors such that the at least one sensor that is selected is most appropriate for the wearer and for measuring the at least one first parameter,
   wherein the wearer data comprises at least morphology data relating to morphology of contact areas of the wearer, or contact areas of the wearer's head or the wearer's wrist, and the mounted sensing device,
   wherein the mounted sensing device further comprises a second set of similar sensors having different location and/or orientation and configured to measure at least one second parameter relating to the wearer of the mounted sensing device, the second parameter being different than the first parameter, and during the selecting at least one sensor from the second set of sensors is selected so that location and/or orientation of the selected at least sensor is a most appropriate of the second set of sensors for the wearer and/or for measuring the at least one second parameter, and
   wherein during the selecting the at least one sensor is selected by measuring the at least one parameter with each of the plurality of sensors and by selecting the sensors providing most accurate measure.

2. The method according to claim 1, wherein the mounted sensing device is a head mounted device.

3. The method according to claim 1, wherein the mounted sensing device is a wrist mounted device.

4. The method according to claim 1, wherein during the selecting the at least one selected sensor is selected based on application data indicative of application of the measured parameter.

5. The method according to claim 1, wherein during the selecting the at least one sensor is selected based on position data indicative to the position of the mounted sensing device relative to the wearer, or the head of the wearer.

6. The method according to claim 1, wherein the sensors comprise sensors, or eye tracking sensors, configured to measure a gazing direction of the wearer and/or an eyelid beat of the wearer and/or a pupil dilation of the wearer.

7. The method according to claim 1, wherein the sensors comprise sensors, or capacitive sensors, configured to measure contact area or a distance between the mounted sensing device and the wearer, or the wearer's head.

8. The method according to claim 1, wherein the sensors comprise sensors, or resistive sensors, configured to measure biological and/or physiological parameters of the wearer.

9. A non-transitory computer readable medium comprising a computer program product comprising one or more stored sequences of instructions that are accessible to a processor and which, when executed by the processor, causes the processor to carry out the method according to claim 1.

10. A mounted sensing device comprising:
a plurality of similar or identical sensors having different locations and/or orientations, each of the sensors configured to measure at least one parameter relating to a wearer of the mounted sensing device;
a non-transitory computer-readable medium according to claim 9; and
program instructions stored on the non-transitory computer-readable medium and executable by at least one processor to select at least one of the sensors having a location and/or orientation most appropriate out of the sensors for the wearer and for measuring the at least one parameter based on wearer data indicative of morphology of the wearer,
wherein during the selecting of at least one of the sensor, a distribution of measurement frequencies implemented by each sensor is determined based at least on the at least one parameter intended to be measured, and
wherein the wearer data comprises at least morphology data relating to morphology of contact areas of the wearer, contact areas of the wearer's head or the wearer's wrist, and the mounted sensing device.

11. The mounted sensing device according to claim 10, further comprising a communication unit configured to receive an application data indicative of application of the measured parameter,
wherein the processor is further configured to select a most appropriate sensor based on the application data,
wherein the communication unit communicates with one or more other communication units by way of a communication network, and
wherein the communication network is based on Internet, including Web servers, file servers, and media servers.

12. The mounted sensing device according to claim 10, wherein the mounted sensing device is a head mounted device.

13. The mounted sensing device according to claim 10, wherein the mounted sensing device is a wrist mounted device.

14. The mounted sensing device according to claim 11, wherein the devices communicate via hypertext transfer protocol (HTTP).

* * * * *